United States Patent
Balusamy

(10) Patent No.: US 10,052,163 B2
(45) Date of Patent: Aug. 21, 2018

(54) ASSISTING A SURGEON TO OPERATE A SURGICAL DEVICE

(71) Applicant: HCL Technologies Limited, Noida (IN)

(72) Inventor: Dorairaj Balusamy, Chennai (IN)

( * ) Notice: Subject to any disclaimer, the term of this patent is extended or adjusted under 35 U.S.C. 154(b) by 0 days.

(21) Appl. No.: 15/651,525

(22) Filed: Jul. 17, 2017

(65) Prior Publication Data

US 2018/0021093 A1 Jan. 25, 2018

(30) Foreign Application Priority Data

Jul. 19, 2016 (IN) .............................. 201611024671

(51) Int. Cl.
| | | |
|---|---|---|
| *A61B 34/20* | (2016.01) | |
| *A61B 34/30* | (2016.01) | |
| *A61B 34/00* | (2016.01) | |

(52) U.S. Cl.
CPC .............. *A61B 34/20* (2016.02); *A61B 34/30* (2016.02); *A61B 34/70* (2016.02); *A61B 2034/2046* (2016.02); *A61B 2034/2048* (2016.02)

(58) Field of Classification Search
CPC ......... A61B 34/20; A61B 34/30; A61B 34/70; A61B 17/1671; A61B 17/1703; A61B 2034/2072; A61B 2017/00119; A61B 2034/2046; A61B 34/2046
See application file for complete search history.

(56) References Cited

U.S. PATENT DOCUMENTS

| 7,366,562 | B2 | 4/2008 | Dukesherer et al. |
| 7,492,930 | B2 | 2/2009 | Leitner et al. |
| 8,057,479 | B2 | 11/2011 | Stone |
| 8,974,468 | B2 | 3/2015 | Borja |
| 9,283,048 | B2 | 3/2016 | Kostrzewski et al. |
| 9,687,301 | B2 * | 6/2017 | Lee ........................ A61B 34/37 |
| 9,782,229 | B2 * | 10/2017 | Crawford ............... A61B 34/30 |
| 2005/0193451 | A1 * | 9/2005 | Quistgaard .......... A61B 5/6843 414/1 |

(Continued)

OTHER PUBLICATIONS

Chengkuo Lee et. al., "MEMS tri-axial force sensor with an integrated mechanical stopper for guidewire applications", Microsyst Technol (2013).

*Primary Examiner* — An T Nguyen
(74) *Attorney, Agent, or Firm* — HM Law Group LLP; Vani Moodley

(57) ABSTRACT

The present disclosure relates to system(s) and method(s) for assisting a surgeon to operate a surgical device. The system is configured to receive real-time spatial data corresponding to a set of movable arms of a surgical device. In one embodiment, each tag may be enabled to capture the real-time spatial data by a set of sensors deployed on each tag with precise coordinate markings. Further, the system receive reference spatial data corresponding to each of the set of movable arms pertaining to the surgical device. The system is configured to compare the real-time spatial data with the reference spatial data to generate a matching score corresponding to each movable arm. The system is configured to identify one or more movable arms, from the set of movable arms with a matching score greater than a predefined threshold score and generate an alert corresponding to the one or more movable arms.

11 Claims, 3 Drawing Sheets

(56) References Cited

U.S. PATENT DOCUMENTS

| | | | |
|---|---|---|---|
| 2010/0312103 A1* | 12/2010 | Gorek | A61B 6/12 600/425 |
| 2011/0119224 A1* | 5/2011 | Mangione-Smith | A61B 6/12 706/52 |
| 2013/0138599 A1* | 5/2013 | Mangione-Smith | A61B 6/12 706/52 |
| 2013/0345718 A1* | 12/2013 | Crawford | A61B 17/025 606/130 |
| 2015/0327948 A1* | 11/2015 | Schoepp | A61B 5/061 600/424 |
| 2016/0022374 A1 | 1/2016 | Haider et al. | |
| 2016/0066913 A1* | 3/2016 | Swayze | A61B 17/072 227/176.1 |
| 2016/0354162 A1* | 12/2016 | Yen | A61B 34/20 |
| 2017/0188011 A1* | 6/2017 | Panescu | H04N 13/025 |
| 2017/0238946 A1* | 8/2017 | van der Walt | A61B 17/1707 |
| 2017/0245780 A1* | 8/2017 | Selover | A61B 5/061 |
| 2017/0252921 A1* | 9/2017 | Hynna | B25J 9/161 |
| 2017/0296189 A1* | 10/2017 | Vendely | A61B 17/068 |

* cited by examiner

ASSISTING A SURGEON TO OPERATE A SURGICAL DEVICE

CROSS-REFERENCE TO RELATED APPLICATIONS AND PRIORITY

The present application claims priority from Indian Patent Application No. 201611024671 filed on 19 Jul. 2016 the entirety of which is hereby incorporated by reference.

TECHNICAL FIELD

The present disclosure in general relates to the field of surgical device. More particularly, the present invention relates to a system and method for assisting a surgeon to operate a surgical device.

BACKGROUND

With increased availability of technology based solutions for various medical applications, the need for precision in medical surgical procedures are becoming critical for predictable results. Further there are numerous medical devices that are already approved and being used in field, that do not have intelligence.

Though, pure mechanical surgical tools have its utilitarian benefits of less maintenance and complexity compared to an electro-mechanical device, with technology solution availability, the benefits of simplicity are becoming a bottleneck to introduce sensor based intelligence and provide value added features to a pure mechanical device. Also without the use of sensor based intelligence making permanent design changes to a mechanical tool may prove time consuming and high cost may be involved.

SUMMARY

This summary is provided to introduce aspects related to systems and methods for assisting a surgeon to operate a surgical device and the aspects are further described below in the detailed description. This summary is not intended to identify essential features of the claimed subject matter nor is it intended for use in determining or limiting the scope of the claimed subject matter.

In one embodiment, a system for assisting a surgeon to operate a surgical device is illustrated. The system comprises a processor coupled to a memory, wherein the processor is to execute programmed instructions stored in the memory. The processor may be configured to execute a programmed instruction stored in the memory for receiving real-time spatial data corresponding to a set of movable arms of a surgical device. The real-time spatial data may be captured by enabling a set of tags attached to the set of movable arms of the surgical device. In one embodiment, each tag may be enabled to capture the real-time spatial data by a set of sensors deployed on each tag. Further, the processor may be configured to execute a programmed instruction stored in the memory for receiving reference spatial data corresponding to each of the set of movable arms pertaining to the surgical device. Further, the processor may be configured to execute a programmed instruction stored in the memory for comparing the real-time spatial data with the reference spatial data to generate a matching score corresponding to each movable arm. Further, the processor may be configured to execute a programmed instruction stored in the memory for identifying one or more movable arms, from the set of movable arms with a matching score greater than a predefined threshold score. Further, the processor may be configured to execute a programmed instruction stored in the memory for generating an alert corresponding to the one or more movable arms, wherein the alert indicates that the one or more movable arms are not operated as per predefined guidelines, thereby assisting a surgeon to operate the surgical device.

In one embodiment, a method for assisting a surgeon to operate a surgical device is illustrated. The method may comprise receiving real-time spatial data corresponding to a set of movable arms of a surgical device. The real-time spatial data may be captured by enabling a set of tags attached to the set of movable arms of the surgical device. In one embodiment, each tag may be enabled to capture the real-time spatial data by a set of sensors deployed on each tag. The method may further comprise receiving reference spatial data corresponding to each of the set of movable arms pertaining to the surgical device. The method may further comprise comparing the real-time spatial data with the reference spatial data to generate a matching score corresponding to each movable arm. The method may further comprise identifying one or more movable arms, from the set of movable arms with a matching score greater than a predefined threshold score. The method may further comprise generating an alert corresponding to the one or more movable arms, wherein the alert indicates that the one or more movable arms are not operated as per predefined guidelines, thereby assisting a surgeon to operate the surgical device.

In one embodiment, a non-transitory computer readable medium embodying a program executable in a computing device for assisting a surgeon to operate a surgical device is illustrated. The program comprises a program code for receiving real-time spatial data corresponding to a set of movable arms of a surgical device. The real-time spatial data may be captured by enabling a set of tags attached to the set of movable arms of the surgical device. In one embodiment, each tag may be enabled to capture the real-time spatial data by a set of sensors deployed on each tag. The program comprises a program code for receiving reference spatial data corresponding to each of the set of movable arms pertaining to the surgical device. The program comprises a program code for comparing the real-time spatial data with the reference spatial data to generate a matching score corresponding to each movable arm. The program comprises a program code for identifying one or more movable arms, from the set of movable arms with a matching score greater than a predefined threshold score. The program comprises a program code for generating an alert corresponding to the one or more movable arms, wherein the alert indicates that the one or more movable arms are not operated as per predefined guidelines, thereby assisting a surgeon to operate the surgical device.

BRIEF DESCRIPTION OF DRAWINGS

The detailed description is described with reference to the accompanying figures. In the figures, the left-most digit(s) of a reference number identifies the figure in which the reference number first appears. The same numbers are used throughout the drawings to refer like features and components.

DETAILED DESCRIPTION

Figure 1:
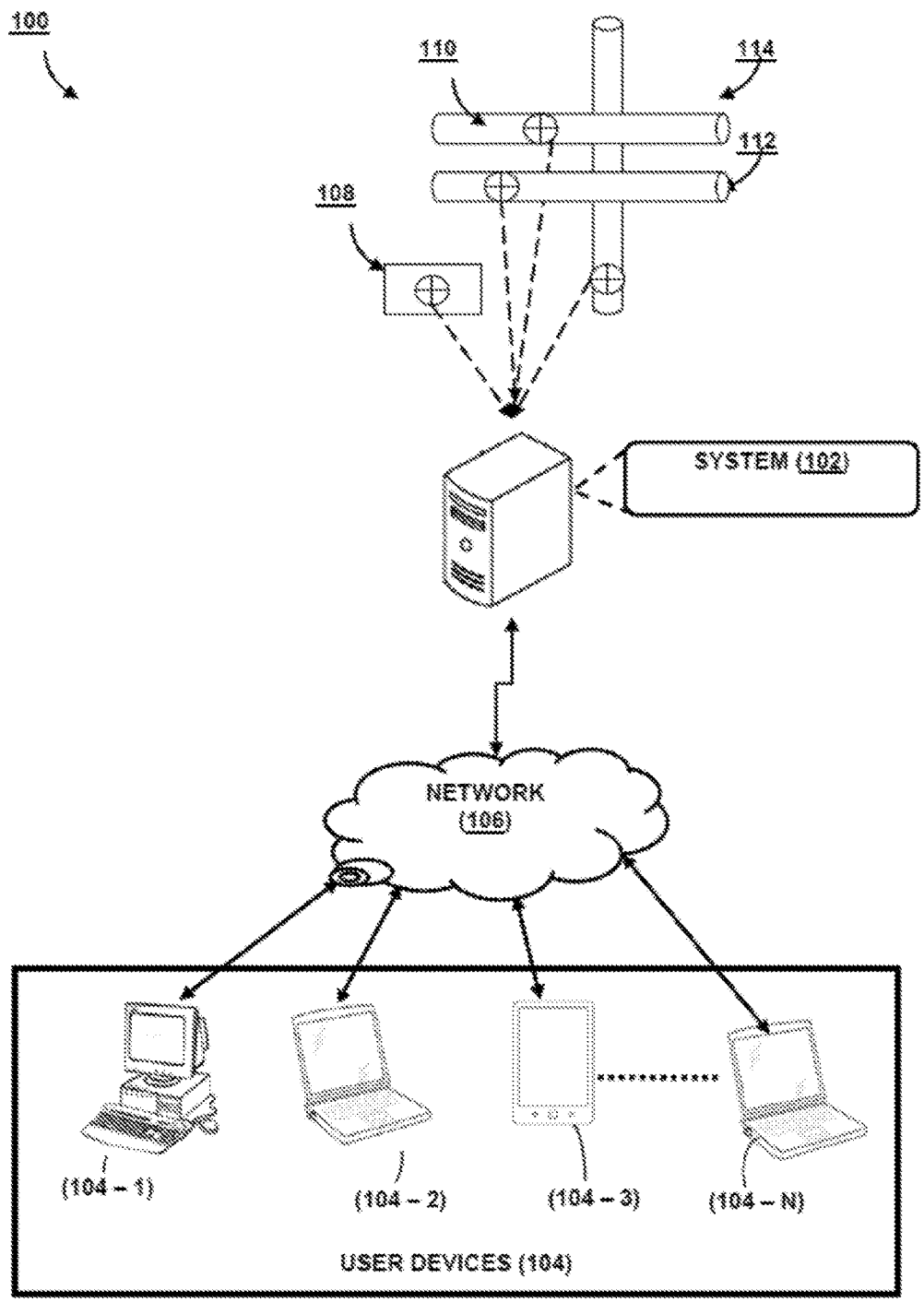
FIG. 1 illustrates a network implementation of a system for assisting a surgeon to operate a surgical device, in accordance with an embodiment of the present subject matter.

The present disclosure relates to a system and method for assisting a surgeon to operate a surgical device. In one embodiment, a set of tags may be attached to each movable arm of the surgical device. The tag may be in the form of an electronic adhesive patch or an electronic sticker with printed coordinate markers. The printed coordinate markers may be used to stick the tag at a predefined marked location on the movable arm. The electronic adhesive patch/tag is enabled with a set of sensors to capture real-time spatial data associated with the movement of the movable arm. The set of sensors may include an accelerometer sensor, a magnetometer sensor, a gyroscopic sensor, and a proximity sensor for capturing the real-time spatial data. In one embodiment, the tag may be of different geometric shapes and may have a coordinate markers printed on to it that can be fixed on a predetermined free space location of the movable arms of the surgical device. By fixing the set of tags, real-time spatial data may be captured from the movable arms of the surgical device. The real-time spatial data may include acceleration, orientation, rotational and proximity based real time spatial data with reference to an external reference spatial point, which is critical for procedures where movement of handheld surgical device is used for patient treatment efficacy and safety.

In one embodiment, the real-time spatial data corresponding to x, y, and z coordinates may be stored in a database for a specific use cycle and later retrieved for analyzing the real-time usage data for product and industrial design engineers to study the quantifiable human usage factor parameters in real time for training and bettering the product design incrementally. In one embodiment, the set of tags affixed to the surgical device are configured to connect with the system and transmit the real-time spatial data. The real-time spatial data may be analyzed by the system in order to generate audio or visual instructions for guiding an operator of the surgical device to operate the surgical device. In one embodiment, the real-time spatial data may be captured by the system through a wireless communication channel enabled between the set of tags and the system.

In one embodiment, the distance between the set of patches is predefined based on the dimensional information of each movable arm. In one embodiment, two or more tags on the surgical device separated by a predetermined distance may act in tandem along with the system as well as between each other to provide relative positional movement data/spatial data. This spatial data may include, acceleration, orientation, rotational and proximity based real time information with reference to an external reference spatial point, which is critical for procedures where movement of handheld surgical device is used for patient treatment efficacy and safety.

The spatial data captured from the set of tags may be compared with historical usage data by the system in order to generate alerts/notifications for guiding the user in performing the surgery. The spatial data may also be used in improving the design of the surgical device.

In one embodiment, the system may be configured to perform the following actions:

Tag calibration and registration:

At this stage, once the tag is affixed to the movable arm of the surgical device, the tags are calibrated by keeping the surgical device without movement for a predetermined duration. In one embodiment, the spatial data captured from the set of tags also includes tolerance data introduced due to environmental vibrations.

Further, the tags are configured to communicate with other tags and register the relative coordinates. This is performed in order to track the future relative movement of the movable arms.

The system is configured to follow predefined protocols for communication between two or more patches and the communication between the patches and the system.

Tag communication:

The set of tags may communicate with each other and the system using Bluetooth or other low energy data communication channels.

Patch data acquisition and coordination:

Each tag from the set of tags may be configured to acquire 3-axis coordinate information like acceleration, orientation, rotation and proximity information and communicate with each other. A pre configuration of the tag may be required from an external computer depending on the configuration. The acquired data can be communicated with each other depending upon the pre-configuration. The relative difference between the spatial and angular readings may provide the data of interest for taking decision for the relevant use case under which the tag solution may be used.

Data presentation and use:

The real-time spatial data once captured may be used in order to guide the user in performing surgery. For example, the data may be used in order to generate audible signal and visual signal for alerting the users to in terms of spatial/angular margins to be followed while operating the surgical device. Further, the system may also track and provide a visual representation of the patches for the user to correct the physical movements.

While aspects of described system and method for assisting a surgeon to operate a surgical device may be implemented in any number of different computing systems, environments, and/or configurations, the embodiments are described in the context of the following exemplary system.

Referring now to FIG. 1, a network implementation 100 of a system 102 for assisting a surgeon to operate a surgical device is disclosed. Although the present subject matter is explained considering that the system 102 is implemented on a server, it may be understood that the system 102 may also be implemented in a variety of computing systems, such as a laptop computer, a desktop computer, a notebook, a workstation, a mainframe computer, a server, a network server, and the like. In one implementation, the system 102 may be implemented in a cloud-based environment. It will be understood that the system 102 may be accessed by a primary user through one or more user devices 104-1, 104-2 . . . 104-N, collectively referred to as user devices 104 hereinafter, or applications residing on the user devices 104. Examples of the user devices 104 may include, but are not limited to, a portable computer, a personal digital assistant, a handheld device, and a workstation, file server, version control servers, bugs tracking servers. The user devices 104 are communicatively coupled to the system 102 through a network 106.

In one implementation, the network 106 may be a wireless network, a wired network or a combination thereof. The network 106 can be implemented as one of the different types of networks, such as intranet, local area network (LAN), wide area network (WAN), the internet, and the like. The network 106 may either be a dedicated network or a shared network. The shared network represents an association of the different types of networks that use a variety of protocols, for example, Hypertext Transfer Protocol (HTTP), Transmission Control Protocol/Internet Protocol (TCP/IP), Wireless Application Protocol (WAP), and the like, to communicate with one another. Further the network 106 may include a variety of network devices, including routers, bridges, servers, computing devices, storage devices, and the like.

Further, the system 102 is configured to connect with a set of tags 110 mounted on a set of movable arms 112 of a surgical device 114. In one embodiment, each tag from the set of tags 110 is configured to capture real-time spatial data corresponding to the movement of the corresponding movable arm. The real-time spatial data may be captured with reference to a fixed point 108. Once the spatial data corresponding to the set of movable arms 112 is captured. In the next step, this spatial data is compared with reference spatial data in order generate alerts for the surgeon and guide the surgeon to perform the surgery. The process of assisting a surgeon to operate a surgical device is further elaborated with respect to FIG. 2.

Figure 2:
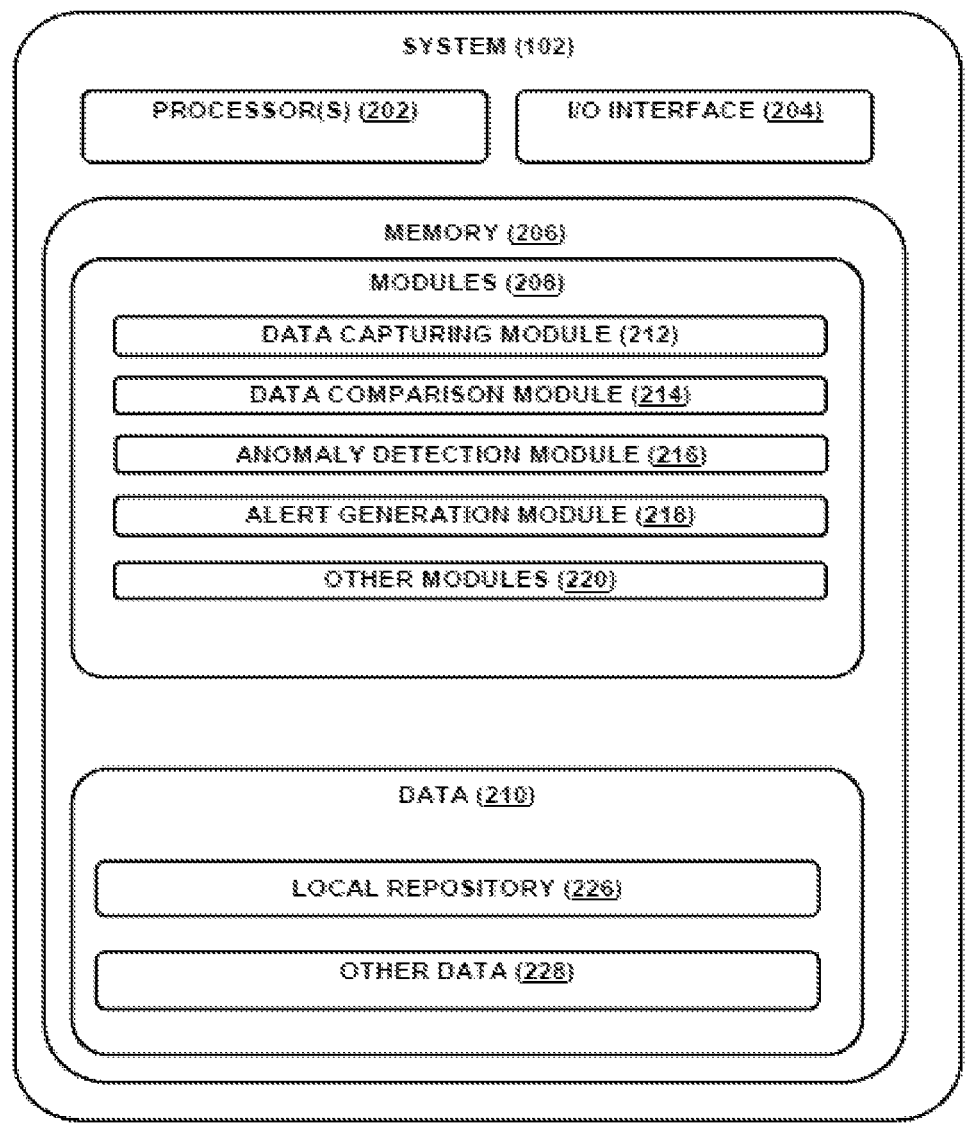
FIG. 2 illustrates the system for assisting a surgeon to operate a surgical device, in accordance with an embodiment of the present subject matter.

Referring now to FIG. 2, the system 102 is illustrated in accordance with an embodiment of the present subject matter. In one embodiment, the system 102 may include at least one processor 202, an input/output (I/O) interface 204, and a memory 206. The at least one processor 202 may be implemented as one or more microprocessors, microcomputers, microcontrollers, digital signal processors, central processing units, state machines, logic circuitries, and/or any devices that manipulate signals based on operational instructions. Among other capabilities, the at least one processor 202 is configured to fetch and execute computer-readable instructions stored in the memory 206.

The I/O interface 204 may include a variety of software and hardware interfaces, for example, a web interface, a graphical user interface, and the like. The I/O interface 204 may allow the system 102 to interact with a user directly or through the user devices 104. Further, the I/O interface 204 may enable the system 102 to communicate with other computing devices, such as web servers and external data servers (not shown). The I/O interface 204 can facilitate multiple communications within a wide variety of networks and protocol types, including wired networks, for example, LAN, cable, etc., and wireless networks, such as WLAN, cellular, or satellite. The I/O interface 204 may include one or more ports for connecting a number of devices to one another or to another server.

The memory 206 may include any computer-readable medium known in the art including, for example, volatile memory, such as static random access memory (SRAM) and dynamic random access memory (DRAM), and/or non-volatile memory, such as read only memory (ROM), erasable programmable ROM, flash memories, hard disks, optical disks, and magnetic tapes. The memory 206 may include modules 208 and data 210.

The modules 208 include routines, programs, objects, components, data structures, etc., which perform particular tasks, functions or implement particular abstract data types. In one implementation, the modules 208 may include a data capturing module 212, a data comparison module 214, an anomaly detection module 216, an alert generation module 218, and other modules 220. The other modules 220 may include programs or coded instructions that supplement applications and functions of the system 102. The data 210, amongst other things, serves as a repository for storing data processed, received, and generated by one or more of the modules 208. The data 210 may also include a local repository 226, and other data 228. The local repository 226 is configured to store spatial data received from the set of tags 112.

In one embodiment, the data capturing module 212 may be configured for receiving real-time spatial data corresponding to the set of movable arms 112 of a surgical device 114. The real-time spatial data may be captured by enabling the set of tags 110 attached to the set of movable arms 112 of the surgical device 114. In one embodiment, each tag may be enabled to capture the real-time spatial data by a set of sensors deployed on each tag. The set of sensors may include an accelerometer sensor, a gyroscope sensor, a magnetometer sensor and proximity sensors. In one embodiment, each tag from the set of tags 110 is attached at a predefined location on the one or more movable arms. The predefined location may be determined based on the dimensions associated with the movable arm.

In one embodiment, once the spatial data is captured by the system 102, in the next step, the data capturing module 212 is further configured to fetch reference spatial data corresponding to each of the set of movable arms 112 pertaining to the surgical device 114 from a repository.

Further, the data comparison module 214 is configured to comparing the real-time spatial data with the reference spatial data to generate a matching score corresponding to each movable arm from the set of movable arms 112. The matching score may be determined based on mathematical computations/calibrations. In one embodiment, data comparison module 214 may be configured to build a coordinate database or a repository, where the set of patches and the connected systems stores and learns the relative coordinates movement during the state of non-movement and during use of the device.

Further, the anomaly detection module 216 is configured for identifying one or more movable arms, from the set of movable arms with a matching score greater than a predefined threshold score. In one embodiment, the matching score is computed and compared with the predefined threshold score recursively after a predefined time interval and a new set of sub-set of movable arms may be determined.

Further, the alert generation module 218 is configured to generate an alert corresponding to the one or more movable arms, wherein the alert indicates that the one or more movable arms are not operated as per predefined guidelines. The alerts may be in the form of audio, visual, or vibration signals. The method for assisting a surgeon to operate a surgical device is further illustrated with respect to the block diagram of FIG. 3.

Figure 3:
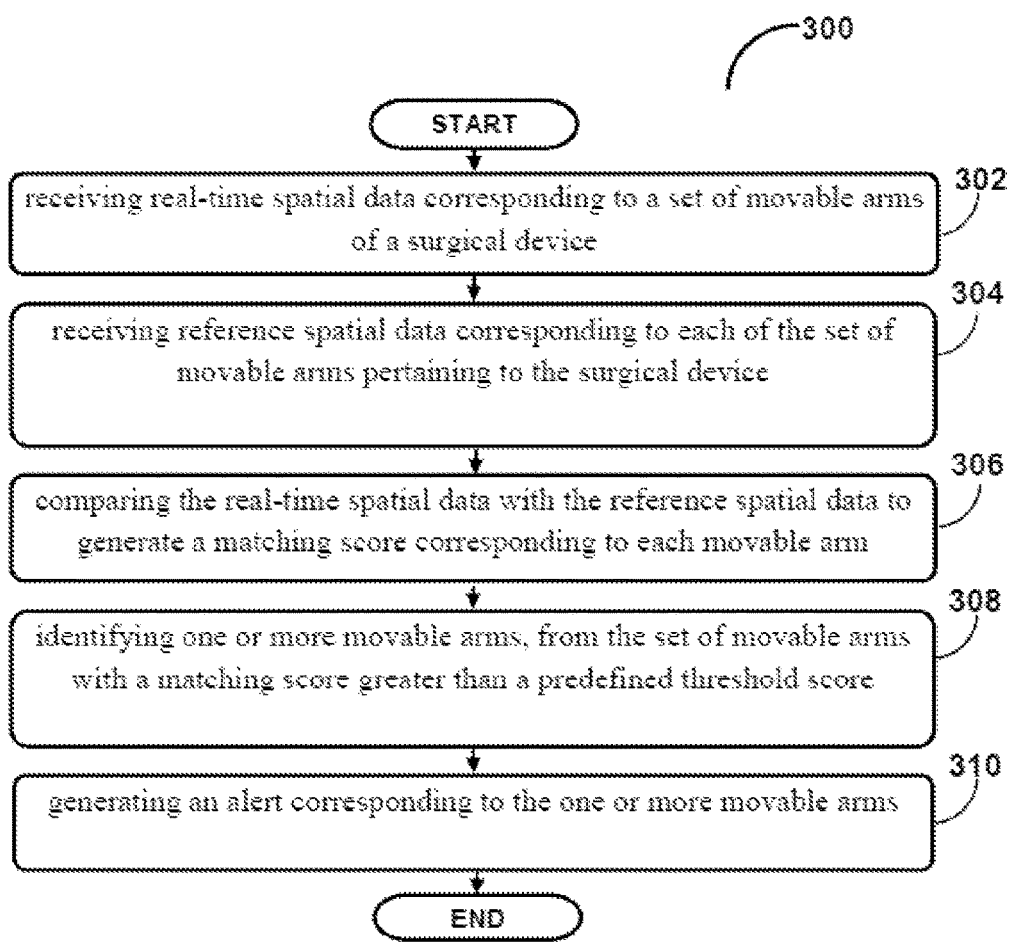
FIG. 3 illustrates a flow diagram for assisting a surgeon to operate a surgical device, in accordance with an embodiment of the present subject matter.

Referring now to FIG. 3, a method 300 for assisting a surgeon to operate a surgical device is disclosed, in accordance with an embodiment of the present subject matter. The method 300 may be described in the general context of computer executable instructions. Generally, computer executable instructions can include routines, programs, objects, components, data structures, procedures, modules, functions, and the like, that perform particular functions or implement particular abstract data types. The method 300 may also be practiced in a distributed computing environment where functions are performed by remote processing devices that are linked through a communications network. In a distributed computing environment, computer executable instructions may be located in both local and remote computer storage media, including memory storage devices.

The order in which the method 300 is described is not intended to be construed as a limitation, and any number of the described method blocks can be combined in any order to implement the method 300 or alternate methods. Additionally, individual blocks may be deleted from the method 300 without departing from the spirit and scope of the subject matter described herein. Furthermore, the method 300 can be implemented in any suitable hardware, software, firmware, or combination thereof. However, for ease of explanation, in the embodiments described below, the method 300 may be considered to be implemented in the above described system 102.

At block 302, the data capturing module 212 may be configured for receiving real-time spatial data corresponding to the set of movable arms 112 of a surgical device 114. The real-time spatial data may be captured by enabling the set of tags 110 attached to the set of movable arms 112 of the surgical device 114. In one embodiment, each tag may be enabled to capture the real-time spatial data by a set of sensors deployed on each tag. The set of sensors may include an accelerometer sensor, a gyroscope sensor, a magnetometer sensor and proximity sensors. In one embodiment, each tag from the set of tags 110 is attached at a predefined location on the one or more movable arms. The predefined location may be determined based on the dimensions associated with the movable arm.

At block 304, once the spatial data is captured, in the next step, the data capturing module 212 is further configured to fetch reference spatial data corresponding to each of the set of movable arms 112 pertaining to the surgical device 114 from a repository.

At block 306, the data comparison module 214 is configured to comparing the real-time spatial data with the reference spatial data to generate a matching score corresponding to each movable arm from the set of movable arms 112. The matching score may be determined based on mathematical computations.

At block 308, the anomaly detection module 216 is configured for identifying one or more movable arms, from the set of movable arms with a matching score greater than a predefined threshold score. In one embodiment, the matching score is computed and compared with the predefined threshold score recursively after a predefined time interval and a new set of sub-set of movable arms may be determined.

At block 310, the alert generation module 218 is configured to generate an alert corresponding to the one or more movable arms, wherein the alert indicates that the one or more movable arms are not operated as per predefined guidelines. The alerts may be in the form of audio, visual, or vibration signals.

Although implementations for methods and systems for assisting a surgeon to operate a surgical device has been described, it is to be understood that the appended claims are not necessarily limited to the specific features or methods described. Rather, the specific features and methods are disclosed as examples of implementations for assisting a surgeon to operate a surgical device.

I claim:

1. A method for assisting a surgeon to operate a surgical device, the method comprising steps of:
    receiving, by a processor, real-time spatial data corresponding to a set of movable arms of a surgical device, wherein the real-time spatial data is captured by a set of tags, wherein one or more tags, from the set of tags, are attached to each movable arm from the set of movable arms of the surgical device, wherein each tag is attached at a predefined location on the movable arm from the set of movable arms based on printed coordinate markers on the tag, wherein the predefined location is determined based on dimensions of the movable arm, wherein each tag is configured to communicate with the set of tags to capture the real-time spatial data, wherein the real-time spatial data corresponds to position of each movable arm relative to the set of movable arms, and wherein each tag is enabled to capture the real-time spatial data by a set of sensors deployed on each tag;
    receiving, by the processor, reference spatial data corresponding to each movable arm from the set of movable arms pertaining to the surgical device;
    comparing, by the processor, the real-time spatial data with the reference spatial data to generate a matching score corresponding to each movable arm;
    identifying, by the processor, one or more movable arms, from the set of movable arms with a matching score greater than a predefined threshold score; and
    generating, by the processor, an alert corresponding to the one or more movable arms, wherein the alert indicates that the one or more movable arms are not operated as per predefined guidelines, thereby assisting a surgeon to operate the surgical device.

2. The method of claim 1, wherein the set of sensors include an accelerometer sensor, a gyroscope sensor, a magnetometer sensor and proximity sensors.

3. The method of claim 1, wherein the predefined location is determined based on the geometrical information of the one or more movable arms.

4. The method of claim 1, wherein the matching score is computed and compared with the predefined threshold score recursively after a predefined time interval.

5. The method of claim 1, wherein the alerts are generated in the form of audio signals, visual signals, and vibration signals.

6. A system for assisting a surgeon to operate a surgical device, the system comprising:
    a memory; and
    a processor, wherein the processor is configured to execute programmed instructions stored in the memory for:
        receiving real-time spatial data corresponding to a set of movable arms of a surgical device, wherein the real-time spatial data is captured by a set of tags, wherein one or more tags, from the set of tags, are attached to each movable arm from the set of movable arms of the surgical device, wherein each tag is attached at a predefined location on the movable arm from the set of movable arms based on printed coordinate marker on the tag, wherein the predefined location is determined based on dimensions of the movable arm, wherein each tag is configured to communicate with the set of tags to capture the real-time spatial data, wherein the real-time spatial data corresponds to position of each movable arm relative to the set of movable arms, and wherein each tag is enabled to capture the real-time spatial data by a set of sensors deployed on each tag;
        receiving reference spatial data corresponding to each movable arm from the set of movable arms pertaining to the surgical device;
        comparing the real-time spatial data with the reference spatial data to generate a matching score corresponding to each movable arm;

identifying one or more movable arms, from the set of movable arms with a matching score greater than a predefined threshold score; and generating an alert corresponding to the one or more movable arms, wherein the alert indicates that the one or more movable arms are not operated as per predefined guidelines, thereby assisting a surgeon to operate the surgical device.

7. The system of claim 6, wherein the set of sensors include an accelerometer sensor, a gyroscope sensor, a magnetometer sensor and proximity sensors.

8. The system of claim 6, wherein the predefined location is determined based on the geometrical information of the one or more movable arms.

9. The system of claim 6, wherein the matching score is computed and compared with the predefined threshold score recursively after a predefined time interval.

10. The system of claim 6, wherein the alerts are generated in the form of audio signals, visual signals, and vibration signals.

11. A non-transitory computer readable medium embodying a program executable in a computing device for assisting a surgeon to operate a surgical device, the computer program product comprising:

a program code for receiving real-time spatial data corresponding to a set of movable arms of a surgical device, wherein the real-time spatial data is captured by a set of tags, wherein one or more tags, from the set of tags, are attached to each movable arm from the set of movable arms of the surgical device, wherein each tag is attached at a predefined location on the movable arm from the set of movable arms based on printed coordinate markers on the tag, wherein the predefined location is determined based on dimensions of the movable arm, wherein each tag is configured to communicate with one or more tags from the set of tags to capture the real-time spatial data, wherein the real-time spatial data corresponds to position of each movable arm relative to the set of movable arms, and wherein each tag is enabled to capture the real-time spatial data by a set of sensors deployed on each tag;

a program code for receiving reference spatial data corresponding to each movable arm from the set of movable arms pertaining to the surgical device;

a program code for comparing the real-time spatial data with the reference spatial data to generate a matching score, corresponding to each movable arm;

a program code for identifying one or more movable arms, from the set of movable arms with a matching score greater than a predefined threshold score; and a program code for generating an alert corresponding to the one or more movable arms, wherein the alert indicates that the one or more movable arms are not operated as per predefined guidelines, thereby assisting a surgeon to operate the surgical device.

* * * * *